US007217289B2

(12) United States Patent
Coronco

(10) Patent No.: US 7,217,289 B2
(45) Date of Patent: May 15, 2007

(54) TREATMENT OF PHOTIC DISTURBANCES IN THE EYE

(76) Inventor: Minas Theodore Coronco, 2 St Pauls Street, Randwick, New South Wales (AU) 2031

( * ) Notice: Subject to any disclaimer, the term of this patent is extended or adjusted under 35 U.S.C. 154(b) by 0 days.

(21) Appl. No.: 10/660,704

(22) Filed: Sep. 12, 2003

(65) Prior Publication Data
US 2005/0060031 A1    Mar. 17, 2005

(51) Int. Cl.
*A61F 2/16* (2006.01)
(52) U.S. Cl. .................. 623/6.17; 351/163; 351/167
(58) Field of Classification Search ...... 623/6.11–6.31, 623/6.2
See application file for complete search history.

(56) References Cited

U.S. PATENT DOCUMENTS

| 4,813,955 | A | * | 3/1989 | Achatz et al. ............. 623/6.17 |
| 5,693,093 | A | * | 12/1997 | Woffinden et al. ......... 623/6.63 |
| 6,129,759 | A | | 10/2000 | Chambers |
| 6,235,055 | B1 | | 5/2001 | Chu |
| 6,280,471 | B1 | * | 8/2001 | Peyman et al. ............ 623/6.17 |
| 6,406,739 | B1 | * | 6/2002 | LeBoeuf et al. ........... 427/2.24 |
| 6,468,306 | B1 | * | 10/2002 | Paul et al. ................. 623/6.16 |
| 6,596,025 | B2 | * | 7/2003 | Portney .................... 623/6.17 |
| 6,884,262 | B2 | * | 4/2005 | Brady et al. ............... 623/6.17 |
| 2003/0144733 | A1 | * | 7/2003 | Brady et al. ............... 623/6.16 |
| 2003/0199976 | A1 | * | 10/2003 | Portney .................... 623/6.17 |
| 2004/0064182 | A1 | * | 4/2004 | Kelman .................... 623/6.17 |

OTHER PUBLICATIONS

Holladay et al, *J. Cataract Ref. Surg.*, 25:748-752 (1999).
Erie et al, *J. Cataract Ref. Surg.*, 27:614-621 (2001).
Masket, *J. Cataract Ref. Surg.*, 26:145-147 (2000).
Ellis et al, *J. Cataract Ref. Surg.*, 27:1061-1064 (2001).
Kohnen et al, *J. Cataract Ref. Surg.*, 27:485-486 (2001).
Kruger et al, *J. Cataract Refract Surg.*, 26:566-570 (2000).
Tester et al, *J. Cataract Ref. Surg.*, 26:810-816 (2000).
Masket et al, *J. Cataract Ref. Surg.*, 19:690-694 (1999).
Davison, *J. Cataract Ref. Surg.*, 26:1346-1355 (2000).
Meacock et al, *Arch. Ophthalmol*, 120:1294-1298 (2002).
Holladay JT, Jang A, Portney V., *Analysis of edge glare phenomena in intraocular lens edge designs*, J Cataract Refract Surg. Jun. 1999; 25(6):748-52.
Coroneo MT, Pham T, Kwok LS, *Off-axis edge glare in pseudophakic dysphotopsia*, J. Cataract Surg. Oct. 2003; 29 (10): 1969-73.
Meacock WR, Spalton DJ, Khan S., *The effect of texturing the intraocular lens edge on postoperative glare symptoms: a randomized, prospective, double-masked study*, Arch Ophthalmol. Oct. 2002; 102(10): 1294-8.
Buehl W, Findl O, Menapace R, Rainer G, Sacu S, Kiss B, Petternel V, Georgopoulos M., *Effect of an acrylic intraocular lens with a sharp posterior optic edge on posteriors capsule opacification*, J Cataract Refract Surg. Jul. 2002; 28(7): 1105-11.

(Continued)

*Primary Examiner*—Suzette Gherbi
(74) *Attorney, Agent, or Firm*—Sughrue Mion, PLLC

(57) ABSTRACT

An ocular lens treated so that at least a portion of the lens perimeter diminishes peripheral light focus on the interior of the eye in use, so as to ameliorate phobic eye disturbances. The lens perimeter of intraocular lenses, artificial corneas and contact lenses are treated to diminish peripheral light focus.

13 Claims, 9 Drawing Sheets

OTHER PUBLICATIONS

Tester R, Pace NL, Samore M, Olson RJ., *Dysphotopsia in phakic and pseudophakic patients: incidence and relation to intraocular lens type*(2). J Cataract Refract Surg. Jun. 2000; 26(6): 810-6.

*Potential Intraocular Lens Designs*, William M. Kirber, Eyeworld.

M. T. Coroneo; Pterygium as and early indicator of ultraviolet insolation: a hypothesis; British Journal of Opthalmology 1993; 77: 734-739.

Minas T. Coroneo, BSc[Med], MB BS, MSc, FRACS, FRACO; Albedo Concentration in the Anterior Eye: A Phenomenon that Locates Some Solar Diseases; Ophthalmic Surgery; Jan. 1990, vol. 21, No. 1.

M. T. Coroneo, N.W. Müller-Stolzenburg and A. Ho; Peripheral Light Focusing by the Anterior Eye and the Ophthalohlioses; Ophthalmic Surgery; Dec. 1991, vol. 22, No. 12.

* cited by examiner 2A                              2B

TREATMENT OF PHOTIC DISTURBANCES IN THE EYE

BACKGROUND OF THE INVENTION

The present invention is directed to ocular lenses, including intraocular lenses, artificial corneas and contact lenses, treated so as to prevent photic disturbances in the eye.

BACKGROUND OF THE INVENTION

Cataract extraction and intraocular lens insertion may be regarded as one of the most successful human body part replacement procedures ever developed. It has been said that "cataract surgery, the most successful procedure in modern medicine, yields outcomes that are unsurpassed by any other surgical procedure" (Obstbaum S. A. "Effective cataract surgery—an undervalued procedure", *J Cataract Refract Surg.* 1998;24: 1417).

The deformable intraocular lens (IOL) was developed in the early 1980s. Formed of polymeric material, IOLs are sufficiently soft and flexible to allow the lens to be folded for insertion into the eye through an incision of reduced size.

IOLs typically incorporate a disk-shaped, transparent lens optic and may include smoothly curved attachment arms referred to as haptics. The lens optic typically is formed of polymeric material such as polymethyl methacrylate, virgin silicon or acrylic based materials, which are suitable for lathe turning or by moulding by injection, compression or cast moulding techniques.

IOL design developments over the years include: square edges to minimise posterior capsular opacity when the IOL is inserted into the posterior capsule of the eye during cataract surgery (Nagata T, Watanabe I. "Optic sharp edge or convexity: comparison of effects on posterior capsular opacification", *Jpn J Ophthalmol,* 1996;40:397–403; Nishi O. et al "Inhibition of migrating lens epithelial cells at the capsular bend created by the rectangular optic edge of a posterior chamber intraocular lens" *Ophthalmic Surg Lasers,* 1998;29:587–94; Nishi O. et al "Preventing posterior capsule opacification by creating a discontinuous sharp bend in the capsule" *J Cataract Refract Surg.,* 1999;25: 521–6.); textured or frosted haptics to increase friction in the interface between tissue and the haptic portions so as to anchor the IOL in the eye (U.S. Pat. No. 6,129,759); and differential anterior and posterior coloration of haptics to facilitate lens orientation for insertion into the eye (U.S. Pat. No. 6,325,055).

Notwithstanding the tremendous developments in cataract treatment, including IOL design, visual disturbances are reported by patients which include glare, streaks and/or dark shadows in the temporal visual field (Nadler D. J, et al "Glare disability in eyes with intraocular lenses" *Am J Ophthalmol* 1984;97:43–47; Masket S. et al "Undesired light images associated with ovoid intraocular lenses" *J Cataract Ref Surg* 1999;19:690–694; Tester R. et al "Dysphotopsia in phakic and pseudophakic patients: incidence and relation to intraocular lens type" *J Cataract Ref Surg* 2000;26:810–816; Häring G. et al "Subjective photic phenomena with refractive multifocal and monofocal intraocular lenses" *J Cataract Ref Surg* 2001;27:245–249; Davidson J. A. "Positive and negative dysphotopsia in patients with acrylic intraocular lenses" *J Cataract Ref Surg* 2000;26: 1346–1355. These visual disturbances may be referred to as "photic disturbances". In the pseudophakic human eye in particular (where the crystalline lens has been surgically removed) photic disturbances (termed pseudophakic dysphotopsia—Tester R. et al in phakic and pseudophakic patients: incidence and relation to intraocular lens type" *J Cataract Ref Surg* 2000;26:810–816) can adversely impact the quality of vision and may affect 7–90% of patients implanted with intraocular lenses (Häring G. et al "Subjective photic phenomena with refractive multifocal and monofocal intraocular lenses" *J Cataract Ref Surg* 2001;27: 245–249; Meacock W. R. et al "The effect of texturing the intraocular lens edge on postoperative glare symptoms. A randomized, prospective, double-masked study" *Arch Ophthalmol* 2002;120:1294–1298.)

Unwanted image formation is a troublesome problem in the pseudophakic eye after IOL insertion. Holliday (Holladay J. T. et al "Analysis of edge glare phenomenon in intraocular lens designs" *J Cataract Ref Surg* 1999;25: 748–752) using ray tracing techniques has investigated the edge glare effects in IOLs. Holliday concluded that rounded edges of the IOL reduce edge glare phenomenon. However, edge glare remains a problem in these conventional designs (Masket S. et al "Undesired light images associated with ovoid intraocular lenses" *J Cataract Ref Surg* 1999; 19:690–694; Tester R. et al "Dysphotopsia in phakic and pseudophakic patients: incidence and relation to intraocular lens type" *J Cataract Ref Surg* 2000;26:810–816; Davidson J. A. "Positive and negative dysphotopsia in patients with acrylic intraocular lenses" *J Cataract Ref Surg* 2000;26: 1346–1355; Meacock W. R. et al "The effect of texturing the intraocular lens edge on postoperative glare symptoms. A randomized, prospective, double-masked study" *Arch Ophthalmol* 2002;120:1294–1298; Holladay J. T. et al "Analysis of edge glare phenomenon in intraocular lens designs" *J Cataract Ref Surg* 1999;25:748–752; Erie J. C. et al "Analysis of postoperative glare and intraocular lens design" *J Cataract Ref Surg* 2001;27:614–21; Masket S. "Truncated edge design, dysphotopsia, and inhibition of posterior capsule opacification" *J Cataract Ref Surg* 2000;26:145–147; Ellis M. F. "Sharp-edged intraocular lens design as a cause of permanent glare" *J Cataract Ref Surg* 2001;27:1061–1064; Kohnen T. "The squared, sharp-edged optic intraocular lens design" *J Cataract Ref Surg* 2001;27: 485–486). Further, such rounded edge designs may be associated with an increased risk of posterior capsular opacification (Kruger A. J. et al "Two year results: sharp versus rounded optic edges on silicone lenses" *J Cataract Refract Surg.,* 2000;26:566–70).

Photic disturbances may also occur in IOLs located outside of the lens capsule, for example for vision correction, with artificial corneas and contact lenses.

This invention is concerned with the problems of photic disturbances associated with ocular lenses, including IOLs, artificial corneas and contact lenses.

SUMMARY OF THE INVENTION

The inventors have found that refracted rays of obliquely instant light may degrade vision in the pseudophakic eye, with oblique or off-axis light from the temporal field posing unexpected optical problems after the crystalline lens has been replaced by an intraocular lens. This is based on their previous findings (Coroneo M. T. et al "Peripheral light focusing by the anterior eye and the ophthalmohelioses" *Ophthalmic Surg.* 1991; 22: 705–711; Maloof A. J. et al "Influence of corneal shape on limbal light focusing" *Invest Ophthalmol Vis Sci.* 1994; 35: 2592–98; Maloof A. J. et al "Anterior segment peripheral light concentration and the crystalline lens" [ARVO Abstract] *Invest Ophthalmol Vis Sci.* 1994; 35: 1327. Abstract nr 332; Coroneo M. T. "Albedo concentration in the anterior eye: a phenomenon that locates some solar diseases" *Ophthalmic Surg* 1990;21:60–6; Kwok L. S. et al "Prevention of the adverse photic effects of peripheral light-focusing using UV-blocking contact lenses" *Invest Ophthalmol Vis Sci.* 2003;44:1501–7; Sliney D. H. "Epidemiological studies of sunlight and cataract: the critical factor of ultraviolet exposure geometry" *Ophthalmic Epidemiol* 1994;1:107–19—who referred to the pioneering work of the inventor as the "Coroneo Effect") in normal eyes that this peripheral light can be refracted and focused by the temporal corneal periphery into locations inside the eye (the phenomenon of peripheral light focusing, PLF). PLF is due to the convexity of the cornea which can concentrate light by up to twenty times affecting the distal cornea and lens.

The inventor has found that the dimensional difference of the IOL compared to the natural lens enables oblique light to strike the nasal perimeter of the IOL and thereafter be focused onto sites in the nasal interior of the eye, including the nasal retina causing photic disturbances such as unwanted image formation. This effect may also occur with the natural lens. Such unwanted image formation can adversely impact the quality of vision in the pseudophakic eye. Known as pseudophakic dysphotopsia (PDP), the visual disturbances reported by patients include glare, streaks and dark shadows in the temporal visual field. The prior art has only contemplated the role of on-axis instant light in PDP formation, and has failed to consider the effects of off-axis oblique incident light (such as 65°–89°) in PDP. Thus, prior art attempts to treat photic disturbances such as PDP have been unsatisfactory.

The inventor has surprisingly found that oblique, off-axis light is further focused by the nasal perimeter of an IOL into intraocular locations, such as the nasal retina, causing photic disturbances.

In accordance with a first aspect of the invention there is provided an ocular lens adapted so that at least a portion of the lens periphery diminishes oblique light focusing on the interior of the eye in use, so as to treat photic disturbances.

In accordance with another aspect of this invention there is provided an intraocular lens configured to reduce or eliminate oblique incident light photic disturbances in the eye, said lens comprising anterior and posterior surfaces defining a central visually transparent lens optic extending from said anterior to said posterior surfaces and a peripheral portion outside of the central lens optic, wherein the optical properties of the peripheral portion are selected such that oblique incident light focusing on said peripheral portion is diminished or refracted laterally or anteriorly as opposed to posteriorly.

The peripheral portion of the lens or a part thereof may include a light absorbing material. Alternatively the lens periphery portion may be treated in any manner which diminishes peripheral light focusing including, for example, laser etching or other laser treatment, treatment with a light absorbing material and deposition of opaque or pigment particles.

Alternatively, the peripheral optics of the intraocular lens are modified such that when struck by oblique incident light, the light is refracted sideways or anteriorly (as opposed to posteriorly) thereby the foci now occur in the ciliary body which is light-insensitive instead of the retina which is light sensitive. This can be achieved by modifying the anterior and or posterior curvature of the intraocular lens such that an effective prismatic effect occurs to achieve the desired refraction of light foci away from the nasal retina.

In accordance with another aspect of the invention there is provided a method for the production of an intraocular lens configured to reduce or eliminate incident light photic disturbances, said lens having an anterior surface and a posterior surface defining a central visually transparent lens optic extending from said anterior surface to said posterior surface and a peripheral portion outside of the central optic, wherein the optical properties of the peripheral portion are selected such that oblique incident light focusing said peripheral portion is minimised, or refracted laterally or anteriorly as opposed to posteriorly.

In accordance with another aspect of the invention there is provided a method for the production of an intraocular lens configured to reduce or eliminate oblique incident light photic disturbances, said lens having an anterior surface and a posterior surface defining a central visually transparent lens optic extending from said anterior to said posterior surface, and a peripheral portion outside of the central lens optic, comprising selecting an anterior surface radius, selecting a posterior surface radius, selecting a centre thickness, selecting a lens diameter and refractive index and calculating ray traces at an angle of incidence of light in the range 71° to 89° and selecting those conditions which focus light laterally or anteriorly.

Other embodiments of the invention are described hereinafter.

DESCRIPTION OF THE PREFERRED EMBODIMENT

Photic disturbances treated according to this invention include one or more of glare, streaks and/or dark shadows in the visual field. Pseudophakic dysphotopsia (PDP) may be avoided according to the present invention.

The inventors have found that adapting or treating at least the peripheral portion of an ocular lens which in use is adjacent to the nasal retina, such that oblique off-axis light is not focused onto the interior of the eye, is effective in the treatment of photic disturbances. In this regard, reference to the "interior of the eye" refers to nasal retinal areas of the eye struck by oblique off-axis light which causes photic disturbances.

In accordance with a first aspect of this invention there is provided an ocular lens adapted so that at least a portion of the lens perimeter diminishes oblique light focusing on the interior of the eye in use, so as to treat photic disturbances.

In accordance with another aspect of this invention there is provided an intraocular lens configured to reduce or eliminate oblique incident light photic disturbances in the eye, said lens comprising anterior and posterior surfaces defining a central visually transparent lens optic extending from said anterior to said posterior surfaces and a peripheral portion (see FIG. 7) outside of the central lens optic, wherein the optical properties of the peripheral portion are selected such that oblique incident light focusing on said peripheral portion is diminished or refracted laterally or anteriorly as opposed to posteriorly.

Figure 7:
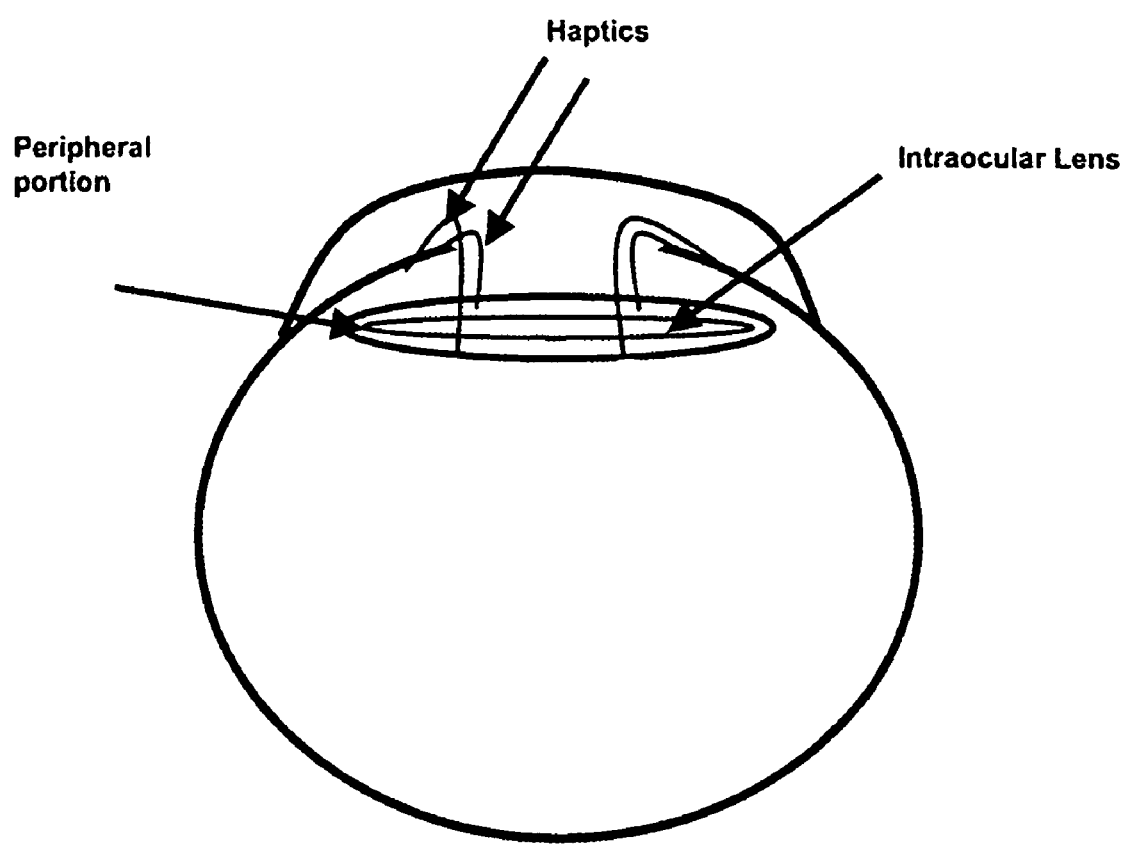
FIG. 7 shows a schematic drawing of an eye in cross section, illustrating an IOL having haptics and a peripheral portion.

Intraocular lenses generally comprise a plate-like or disk shape. The lens has an anterior surface and a posterior surface, which define a visually transparent lens optic extending from said anterior to said posterior surface. These surfaces are generally shaped to obtain the desired optical correction required. The central optic transmits light onto the central area of the retina including the macula. As shown in FIG. 7, the peripheral portion of the lens is that lying outside the central optic, extending from the anterior to anterior surfaces and to the perimeter of the lens. The perimeter of the lens may be referred to as the edge of the lens. The perimeter may have rounded corners or sharp edges, or edge configurations falling therebetween. The perimeter may be stepped or otherwise shaped. The lens optic and peripheral portion may be continuous, that is, formed of the same material and not apparently distinguishable therefrom microscopically. However, the peripheral portion of an IOL does not focus light onto the macula region of the retina.

Figure 1:
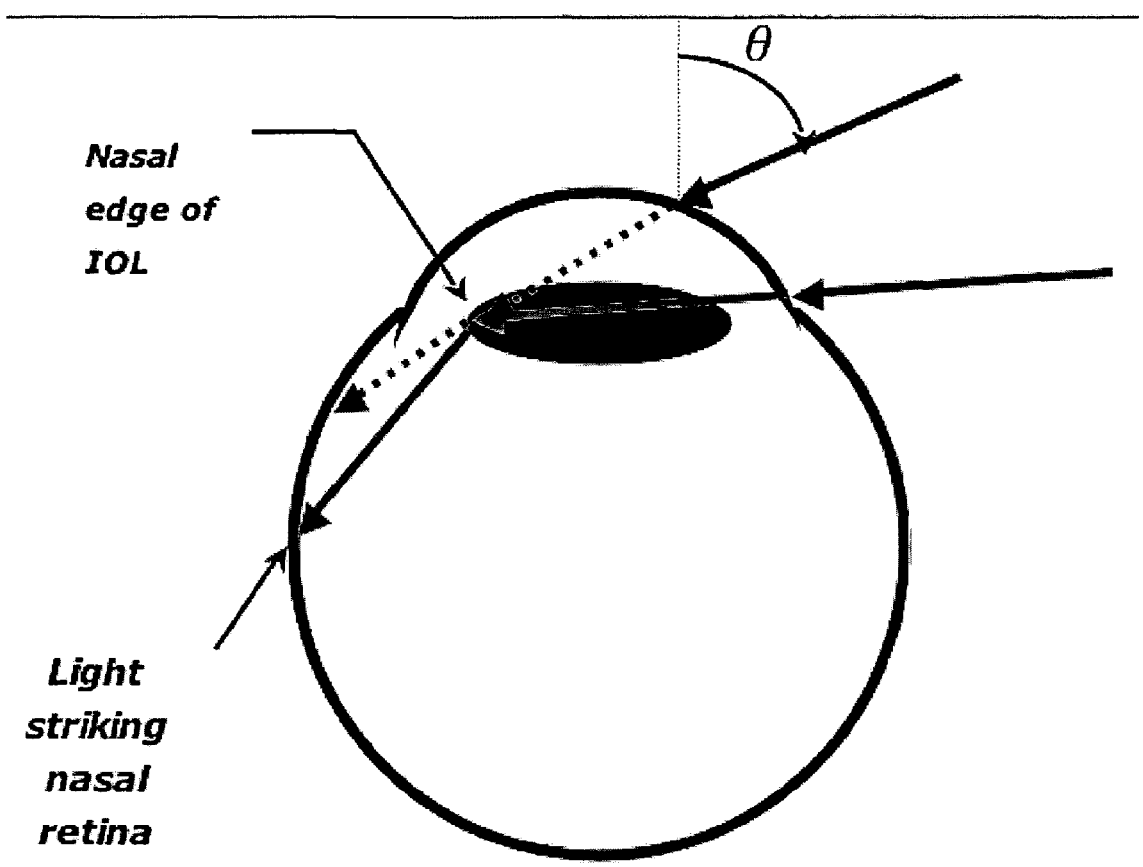
FIG. 1 shows a schematic drawing of an eye in cross-section, showing oblique light striking an IOL at the nasal perimeter or edge and being focused into the eye striking the nasal retina as different areas depending on the angle of incidence (Θ) causing visual disturbance.

The peripheral portion of the lens is adapted to diminish peripheral focusing effects of oblique incident light. This may be achieved using a light absorbing material at the peripheral portion, such as perimeter. For example, a circumferential section of the anterior and/or posterior surface immediately adjacent the perimeter likewise may include a light absorbing material, without effecting visual acuity through the lens. Such material may be applied to the whole of the peripheral portion. Alternatively, it may be applied to the nasally disposed side of the peripheral portion in use (the nasal edge) which is responsible for photic disturbances as shown in FIG. 1. Additionally, such light absorbing material may be applied to the non-nasal edge lens to reduce light transmission across the lens.

Light absorbing material includes colours or tints which absorb light in totality, or substantially absorb light, so as to diminish oblique incident light focusing effects. For example, opaque or dark colours, such as blackening, may be incorporated into the perimeter, and preferably circumferential portions of the anterior and/or posterior surface of the lens immediately adjacent the perimeter during preparation of the lens, for example by methods disclosed in U.S. Pat. No. 4,640,805 (which describes a spin casting technique for accurately limiting colour application to a lens) and as disclosed in U.S. Pat. No. 6,248,161 (where colouration is applied to a casting mould during the casting process) or by other methods known in the art. Alternatively, the lens perimeter may be treated with one more opaque or light absorbing colourants, for example as described in U.S. Pat. Nos. 4,682,402 and 4,704,017 where water and soluble opaque pigment particles are deposited on lens surfaces. Techniques for applying an opaque/light absorbing material or colour to the perimeter include laser printing, screen printing and other known techniques in the art.

Intraocular lenses are formed from polymeric materials as are well known in the art, for example as described in U.S. Pat. Nos. 6,592,621, 6,579,918 and 5,444,106. Examples of such materials include hydrogels and silicones.

In another embodiment, the perimeter of the lens and optionally circumferential sections of the anterior and/or posterior surface adjacent the perimeter may be chemically etched, irradiated or surface modified such as by laser treatment so as to provide a surface which is light absorbing, or otherwise minimises peripheral light focusing. Light scattering approaches, for example by texturing the edge of square edged lenses, scatter light to intraocular locations causing photic disturbances.

In a preferred embodiment, the peripheral optics of the intraocular lens are modified such that when struck by oblique incident light, the light is refracted sideways or anteriorly, as opposed to posteriorly, and onto nasal retinal cells. Refracting light sideways or anteriorly focuses incident light in the ciliary body of the eye which is eye insensitive instead of the retina which is light sensitive. This may be achieved by modifying the anterior and/or posterior curvature of the intraocular lens such that an effective prismatic effect occurs to achieve the desired refraction of light foci away from the nasal retina, particularly forwardly disposed nasal retinal cells in the eye. The anterior and posterior curvature of the lens may be modified in the peripheral portion outside of the central lens optic, or in the alternative, the curvature of the intraocular lens across the lens as a whole may be modified so as to prevent photic disturbances associated with oblique incident light.

Figure 3:
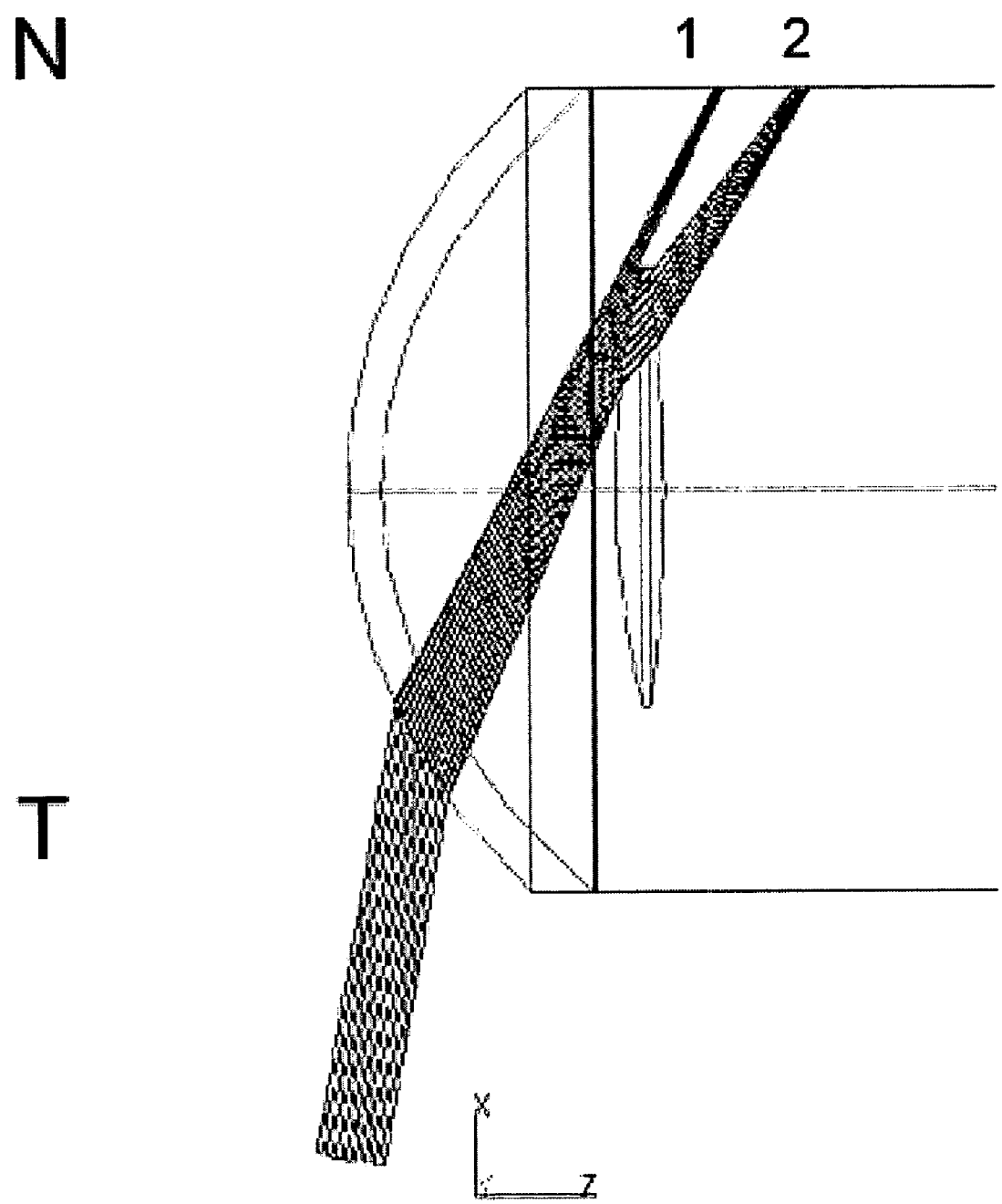
FIG. 3 depicts the output of a calculation showing oblique rays striking temporal limbus (T) and converged by the limbal convexity to intense foci on the nasal side (N) of the eye. In this bundle of rays (incident at an 89° angle to the visual z-axis), many bypass the front of the IOL optic to form focal area 1 while the rest strike the front surface of the IOL optic and are refracted to form focal area 2. Note the penumbra between the two foci

Optical ray tracing to measure refraction of oblique incident light may be conveniently carried out by computer analysis, such as the commercially available OptiCAD® software produced by OptiCAD Corporation, Santa Fe, N.Mex. As shown in FIG. 3 using the OptiCAD program for a given anterior and posterior radius, centre thickness of the lens, diameter and refractive index of the lens material, refraction of such oblique incident light can be precisely calculated. Particular values are selected depending upon the degree of visual correction required in the lens optic, the nature of the material used in the intraocular lens, and other factors of manufacturing choice.

Figure 5:
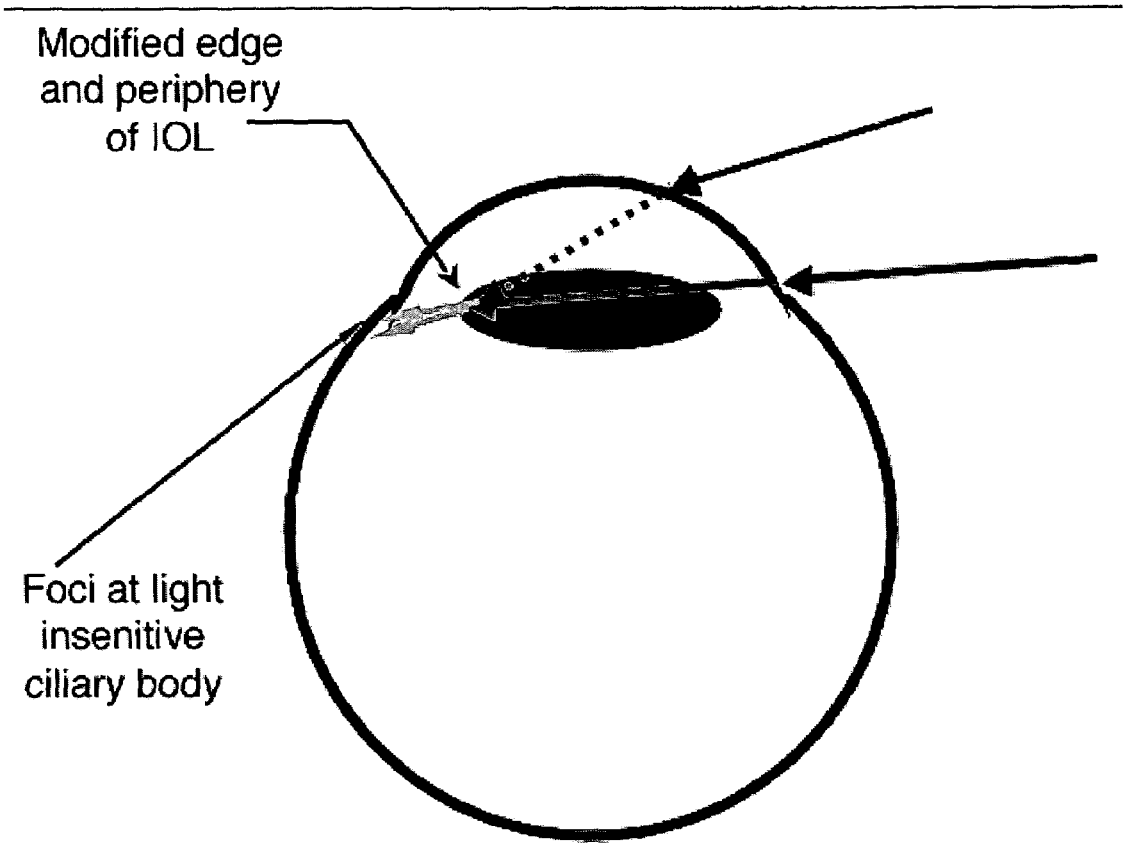
FIG. 5 shows a schematic diagram of an intraocular lens according to an embodiment of the invention.

As shown in FIG. 5, modifying the anterior and/or posterior curvature of the intraocular lens in accordance with this invention enables light to be transmitted away from the nasal retina into the light insensitive ciliary body of the eye.

As shown in FIG. 7, intraocular lenses may include a plurality of elongated, flexible arm haptics projecting outwardly from the lens and configured to engage a predetermined portion of the eye so as to retain the intraocular lens in a predetermined position within the eye. Alternatively, an intraocular lens may be in the form of a plate type having a pair of opposed haptics extending from the lens and moulded together as a one-piece integral construction.

Reference herein to the nasal edge of an ocular lens, such as an IOL, refers to the portion of the intraocular lens proximal to the nasal retina when inserted into the eye.

Anatomically, nasal retinal cells are located in the orbit juxtaposed towards nasal structures, as opposed to the non-nasal edge of an ocular lens disposed at the other side of the lens when located in the eye. The lens optic focuses light onto the centre of the retina at the rear of the eye including the macula. The peripheral portion of an intraocular lens will focus oblique incident light into the nasal interior of the eye, including the nasal retina, which problem is solved by the present invention.

As described herein, and further described in the examples, applicants believe the cause of photic disturbances, particularly pseudophakic dysphotopsia is oblique light which is focused on the nasal perimeter, or nasal edge, of an intraocular lens and focused onto nasal retinal cells of the nasal retina. The inventors believe that scattered and refracted light from the nasal edge of, for example, an intraocular lens causes photic disturbances. The inventors have found that oblique light is concentrated in the order of 2.5 times incident intensity, with peripheral light focusing sustained for angles in the range of about 71°–80°.

The invention will now be described with reference to the following non-limiting examples.

EXAMPLE 1

Oblique Light Focusing and Pseudophakic Dysphotopsia

FIG. 1 shows oblique light striking an IOL at the nasal perimeter or edge and being focused into the eye striking nasal retina. Oblique light incident on the temporal limbus is concentrated at the nasal edge of the intraocular lens. Light rays continue forwards to strike the nasal retina at different areas depending on angle of incidence (⊖). FIG. 1 is based on the following experiments:

Clinical Observation

Figure 2:
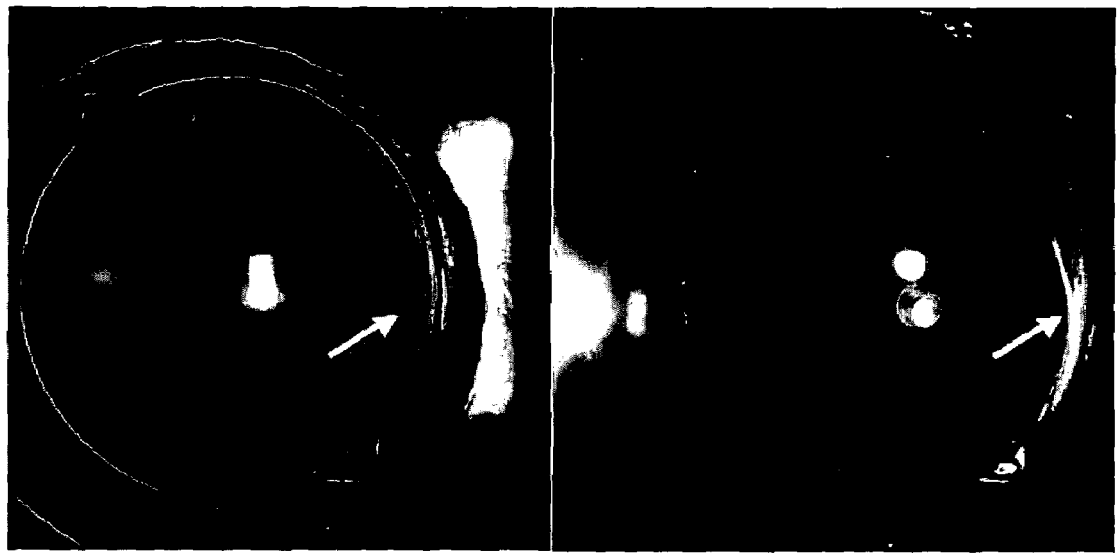
FIG. 2A shows a square edged intraocular lens implanted in a 47 year old patient's right eye.
FIG. 2B shows off-axis light from the temporal visual field elicited a focus of intense light on the nasal aspect of the intraocular lens (arrows) which focuses onto the nasal retina causing visual disturbance.

Using a hand held light source we have been able to induce PDP symptoms in 3 patients referred for second opinions who had developed PDP after having been implanted with square edged intraocular lenses. They described typical photic symptoms at the precise moment when a focus was formed at the nasal edge of their intraocular lens. FIG. 2 shows this focus formed with oblique incident light. FIG. 2A shows a square edged intraocular lens implanted in a 47-year old patient's right eye. Right: Off-axis light from the temporal visual field elicited a focus of intense light on the nasal aspect of the intraocular lens (arrows). This focus continues forward (posteriorly) to strike the nasal retina at different areas depending on the angle of incidence (⊖) as shown in FIG. 1.

Ray Tracing

Using OptiCAD v6.0, an example calculation to model this experiment was undertaken. A representative IOL with an anterior radius of 14.23 mm; posterior radius of 25 mm; centre thickness of 0.72 mm; diameter of 6 mm; refractive index of 1.5597 was chosen. The pupil diameter was assumed to be 5 mm. The ray traces are shown in FIG. 3.

These traces show oblique rays striking temporal limbus (T) which converge by the limbal convexity to intense foci on the nasal side (N) of the eye. In this bundle of rays (incident at an 80° angle to the visual z-axis), many bypass the front of the IOL optic to form focal area 1 while some strike the front surface of the IOL optic and are refracted to form focal area 2. Note the penumbra between the two foci. The penumbra clinically corresponds to dark areas or shadows seen by patients between foci. Thus, modifying the anterior and posterior curvature of the IOL as a whole rather than just in the peripheral portion may be particularly preferred.

Figure 4:
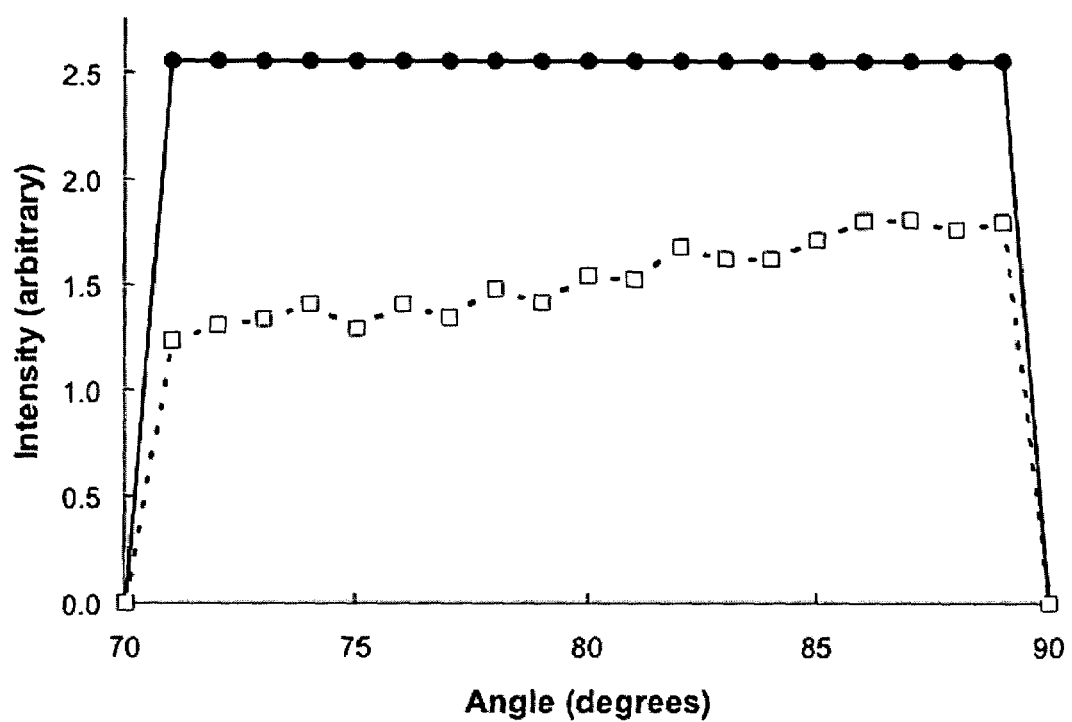
FIG. 4 depicts intensity of focused oblique light at edge of IOL for different angles of incidence at the temporal limbus. (●) Maximum intensity; (□) average intensity compared with incident intensity (value of 1.0).

Light was concentrated by ×2.56 (compared with incident intensity). The PLF effect was sustained for angles of incidence of oblique light in the range 71°–89°. This is depicted in FIG. 4 which depicts intensity of focused oblique light at edge of IOL for different angles of incidence at the temporal limbus. Maximum intensity (●); average intensity (□) are compared with incident intensity (value of 1.0).

FIG. 5 shows an intraocular lens where the anterior and posterior surfaces curvature is selected using OptiCAD® to focus oblique light incident at 71° and 89° laterally or anteriorly into the light insensitive ciliary body.

EXAMPLE 2

Case Studies

This study indicated that depending on the angle of incidence, several secondary images are formed from oblique light. Our findings indicate that some of the images have low intensity and yet may be noticed in photopic conditions. However, under scotopic conditions, such secondary images may become particularly noticeable to the patient and disturb vision.

The oblique light focusing explanation of pseudophakic dysphotopsia in the pseudophakic eye was confirmed with three pseudophakic patients. Using a peripherally placed penlight to focus light onto the nasal aspect of the intraocular lens we were able to precisely reproduce symptoms of arcs of light in the temporal visual field, especially at night.

Figure 6A:
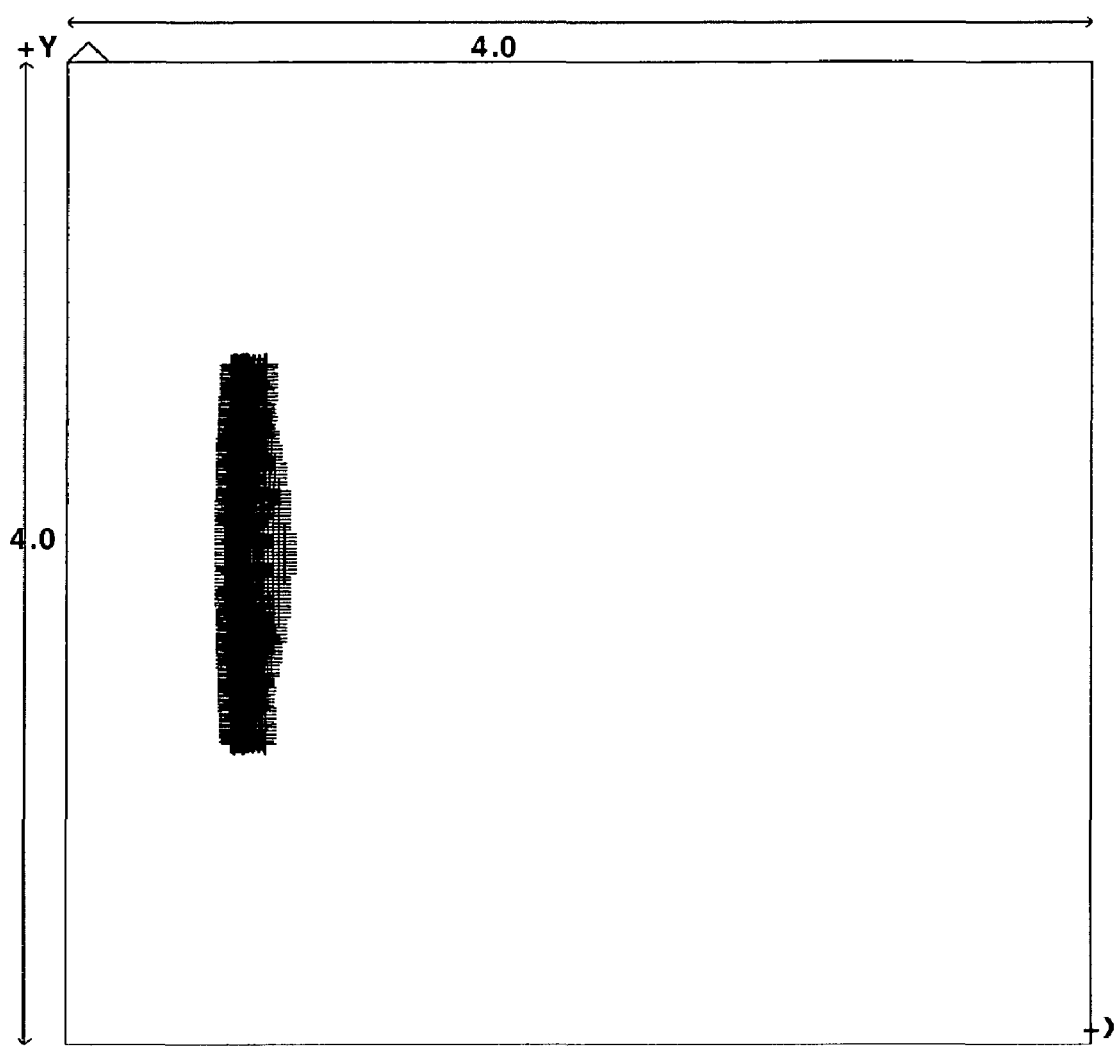
FIGS. 6A–6C shows secondary images formed on the nasal retina of a patient by light bundles at angles of 65° (FIG. 6A), 85° (FIG. 6B) and 92° (FIG. 6C) incidence at the temporal limbus. In all diagrams, the anterior eye is to the right.
Figure 6B:
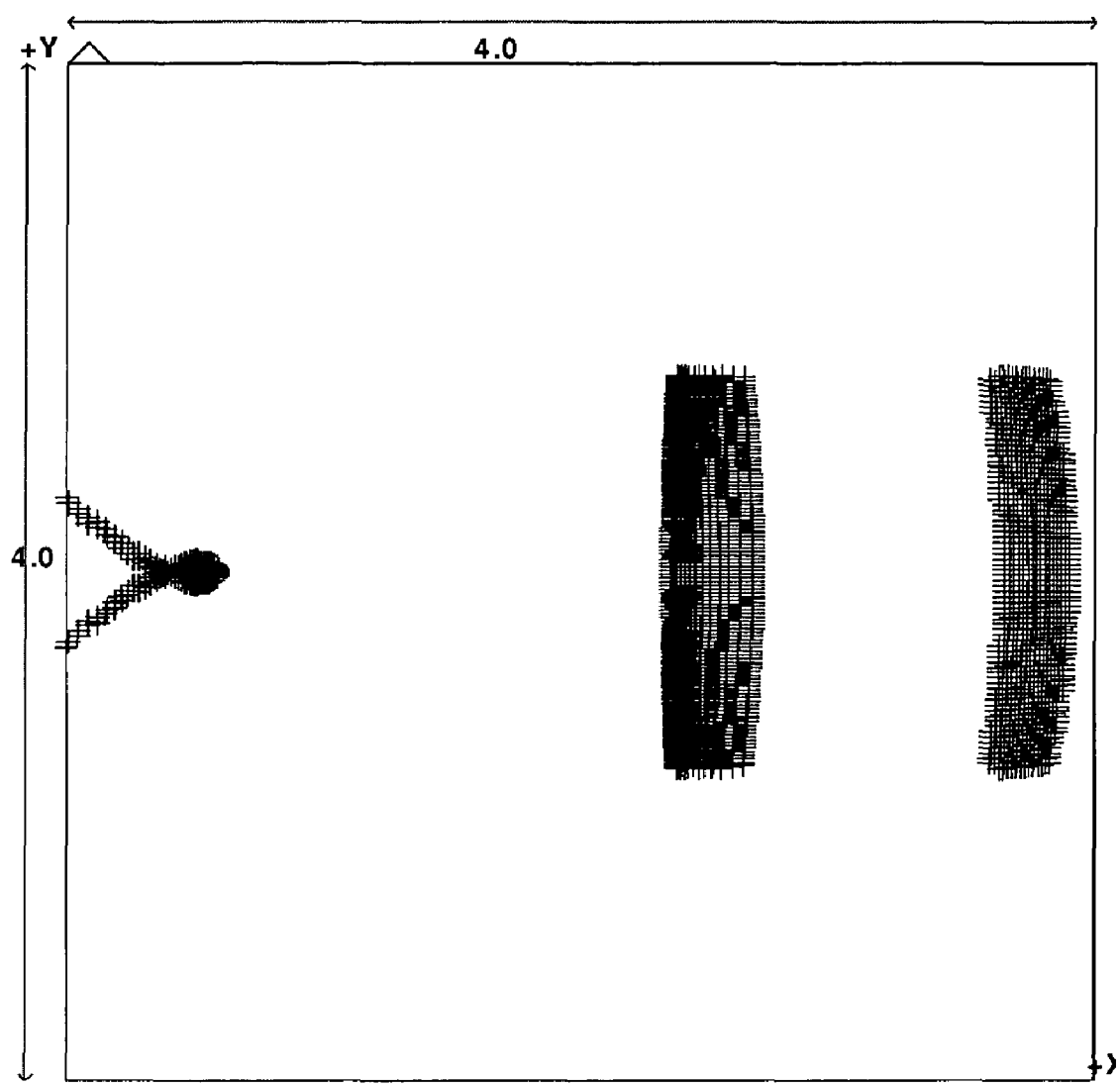
Figure 6C:
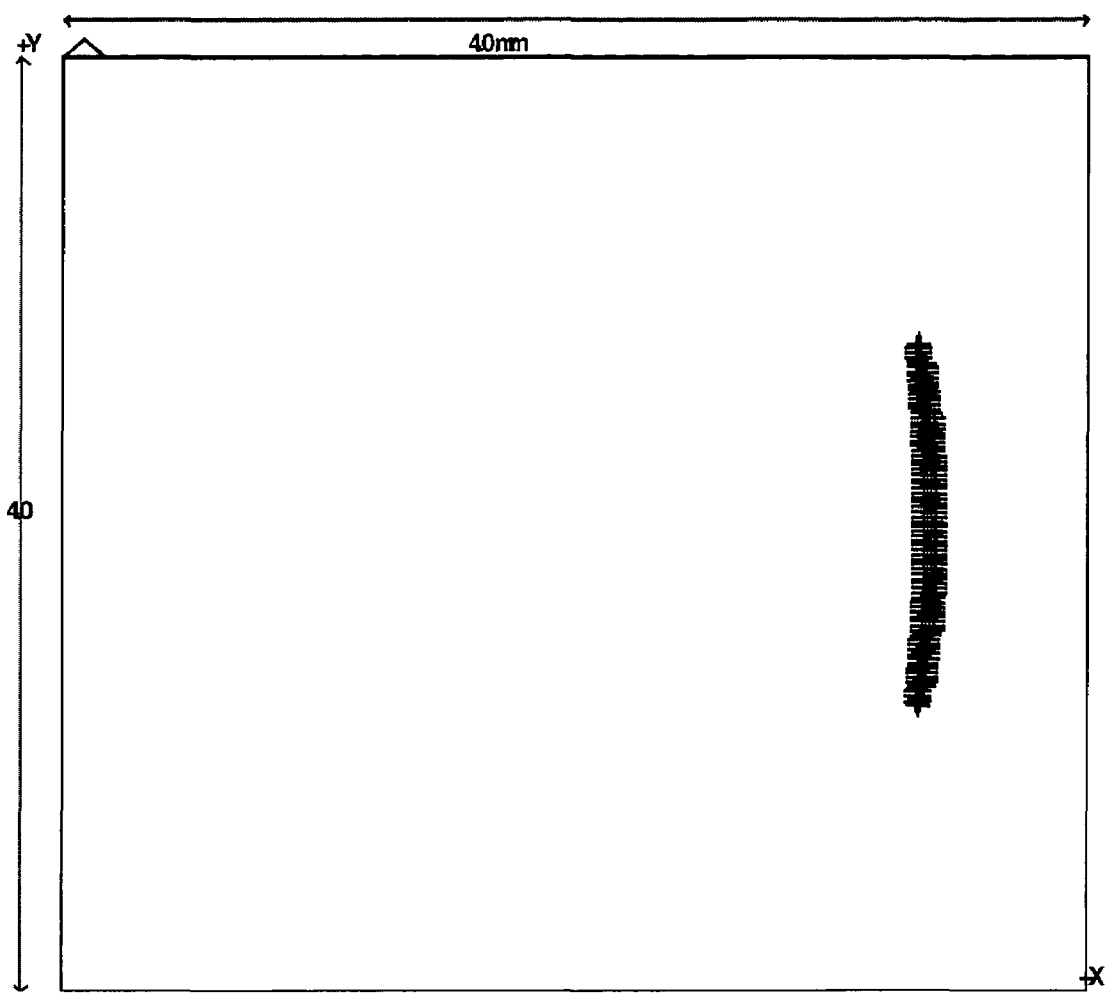

An illustration of this new explanation for pseudophakic dysphotopsia in the pseudophakic eye shown in FIGS. 6A–6C. Secondary images formed on the nasal retina by light bundles at angles of 65° (FIG. 6A), 85° (FIG. 6B) and 92° (FIG. 6C) incidence at the temporal limbus as shown. In all diagrams, the anterior eye is to the right. This 47 year old male had a right cataract surgery and was implanted with a square edged intraocular lens. The patient reported arcs of light in his temporal visual field, the arcs extending up to 180° and blurred vision. These symptoms were particularly noted at night. Using a peripherally placed penlight to focus light on to the nasal aspect of the intraocular lens (FIG. 5) could precisely reproduce his symptoms.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The reference to any prior art in this specification is not, and should not be taken as an acknowledgment or any form of suggestion that that prior art forms part of the common general knowledge in Australia.

The invention claimed is:

1. An intraocular lens configured to reduce or eliminate oblique incident light photic disturbances in the eye, said lens comprising anterior and posterior surfaces defining a central lens optic extending from said anterior to said posterior surfaces and a peripheral portion outside of the central lens optic, wherein at least one of the anterior and posterior surface curvature redirects oblique incident light on the peripheral portion forward of the nasal retina in the eye and onto the ciliary body.

2. An intraocular lens according to claim 1 wherein the peripheral portion of said anterior and said posterior surfaces extends from the central optic to a perimeter of the lens.

3. An intraocular lens according to claim 2 wherein the intraocular lens is disc shaped and said peripheral portion is disposed circumferentially outside the central visually transparent lens optic.

4. An intraocular lens according to claim 1, wherein said peripheral portion is visually transparent.

5. An intraocular lens according to claim 1 wherein said peripheral portion includes a light absorbing material.

6. An intraocular lens according to claim 1 wherein said peripheral portion is treated to diminish peripheral light focusing.

7. An intraocular lens according to claim 6, wherein the lens is treated by laser, or deposition of opaque or light absorbing pigment particles.

8. An intraocular lens according to claim 1 wherein said oblique incident light is in the range 71°–89°.

9. An intraocular lens according to claim 1 wherein the anterior and the posterior surface curvature is adjusted by ray tracing.

10. An intraocular lens according to claim 1, which is foldable.

11. An intraocular lens according to claim 1 or 2 which is an intraocular lens for the treatment of cataract.

12. An intraocular lens according to claim 1 which includes one or more haptics extending from peripheral portion for securing the intraocular lens in the eye.

13. An ocular lens configured to reduce or eliminate oblique incident light photic disturbances in the eye, said lens comprising anterior and posterior surfaces defining a central lens optic extending from said anterior to said posterior surfaces and a peripheral portion outside of the central lens optic, wherein at least one of the anterior and posterior surface curvature redirects oblique incident light on the peripheral portion forward of the nasal retina in the eye onto the ciliary body;

wherein the lens is selected from an intraocular lens, an artificial cornea and a contact lens.

* * * * *